US009029529B2

(12) United States Patent
Dennes et al.

(10) Patent No.: US 9,029,529 B2
(45) Date of Patent: *May 12, 2015

(54) METHODS FOR IMPROVED DNA RELEASE FROM BINDING SUBSTRATES AND/OR DECREASING PCR INHIBITION IN PATHOGEN DETECTION (75) Inventors: T. Joseph Dennes, Parkesburg, PA (US); Michael P. Perry, Downingtown, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 312 days.

This patent is subject to a terminal disclaimer.

(21) Appl. No.: 13/420,158

(22) Filed: Mar. 14, 2012

(65) Prior Publication Data
US 2012/0238739 A1      Sep. 20, 2012

Related U.S. Application Data (60) Provisional application No. 61/452,784, filed on Mar. 15, 2011.

(51) Int. Cl.
*C07H 21/00*    (2006.01)
*C12N 15/10*    (2006.01)

(52) U.S. Cl.
CPC .................................. *C12N 15/1017* (2013.01)

(58) Field of Classification Search
CPC .................................................. C12N 15/1017
See application file for complete search history.

(56) References Cited

U.S. PATENT DOCUMENTS 7,491,495 B2    2/2009    Zielenski et al.

FOREIGN PATENT DOCUMENTS

EP         1637599         3/2006
WO      WO 2004033470     4/2004

OTHER PUBLICATIONS

Degraves Fred J et al: "High-sensitivity quantitative PCR platform", Biotechniques, Informa Life Sciences Publishing, Westborough, MA, US, vol. 34, No. 1, Jan. 1, 2003, pp. 106-110,112, XP002411438, ISSN: 0736-6205.
Hara-Kudo Y et al: "Increased sensitivity in PCR detection of tdh-positive Vibrio parahaemolyticus in seafood with purified template DNA.", Journal of Food Protection, vol. 66, No. 9, Sep. 2003, pp. 1675-1680, ISSN: 0362-028X.
Kolner D E et al: "A high throughput system for the preparation of single stranded templates grown in microculture.", DNA Sequence : The Journal of DNA Sequencing and Mapping 1994 LNKD-PubMed:7987011, vol. 4, No. 4, 1994, pp. 253-257, ISSN: 1042-5179.
Copending International Search Report and Written Opinion of the International Searching Authority in PCT/US2010/044083, issued Jan. 18, 2011.

*Primary Examiner* — Lawrence E Crane (57) ABSTRACT

Disclosed herein are processes for collecting nucleic acids from particulate samples. One embodiment disclosed herein relates to the use of ultrasonic energy to simultaneously shear large nucleic acid molecules and large particulates to very small sizes prior to or during a chemical binding step to a nucleic acid binding surface. Another embodiment involves crushing the nucleic acid binding surface prior to eluting the bound nucleic acid molecules to enable better wetting of the nucleic acid binding surface and easier diffusion of bound nucleic acid molecules out of the nucleic acid binding surface.

14 Claims, 7 Drawing Sheets

Fig. 1

| | | | | |
|---|---|---|---|---|
| ● | ● | ● | ● | 1000 cfu/mL |
| ⊘ | ⊘ | ● | ● | 500 cfu/mL |
| ⊖ | ⊖ | ● | ● | 250 cfu/mL |
| ⊘ | ⊘ | ● | ● | 100 cfu/mL |
| ⊖ | ⊖ | ⊖ | ● | 50 cfu/mL |
| ⊖ | ⊖ | ⊖ | ● | 25 cfu/mL |
| ○ | ○ | ○ | ○ | |
| ○ | ○ | ○ | ○ | |
| Water Bath | | Horn | | |

METHODS FOR IMPROVED DNA RELEASE FROM BINDING SUBSTRATES AND/OR DECREASING PCR INHIBITION IN PATHOGEN DETECTION

CROSS-REFERENCE TO RELATED APPLICATION

This application claims benefit of U.S. Provisional Patent Application No. 61/452,784, filed Mar. 15, 2011, which is incorporated by reference herein in its entirety.

FIELD OF INVENTION

The field relates to a methods for the isolation of nucleic acids contained in particulate samples.

BACKGROUND OF INVENTION

The analysis of samples for microorganisms, such as bacteria, is important for public health. Foods grown, purchased, and consumed by the general population may contain or acquire microorganisms, which flourish or grow as a function of the environment in which they are located. This growth may lead to accelerated spoilage of the food product or the proliferation of pathogenic organisms, which may produce toxins or allergens.

In current testing of foods for pathogens by PCR, the analytical method must be able to detect as little as one organism in 375 g of meat that is incubating in four liters of enrichment broth. In order to be reliably assayed, the pathogen organisms must grow to a concentration of approximately 5,000 organisms per milliliter from which a five microliter sample is collected for the PCR amplification and the detection process. The time consumed for this growth ranges from eight to 24 or more hours. In order to reduce this time, a method is needed that can concentrate the organisms from an incubating broth without introducing the problems related to antibody-antigen interactions.

SUMMARY OF INVENTION

One aspect is for a process for collecting nucleic acids from a particulate sample comprising:
(a) mixing an aliquot of a particulate sample containing nucleic acids with a nucleic acid binding solution;
(b) exposing the mixture of step (a) to ultrasound;
(c) transferring the mixture of step (b) into a device comprising a chamber interior comprising a fibrous nucleic acid binding surface, the chamber interior being capable of expanding in size in at least one dimension; the fibers of the fibrous nucleic acid binding surface expanding to at least partially fill the chamber interior upon wetting with the mixture;
(d) expelling the mixture from the device by compression of the fibrous nucleic acid binding surface while retaining the fibrous nucleic acid binding surface in the chamber interior;
(e) transferring an aliquot of elution buffer into the device;
(f) mixing the elution buffer with the fibrous nucleic acid binding surface; and
(g) expelling the elution buffer from the device by compression of the fibrous nucleic acid binding surface while retaining the fibrous nucleic acid binding surface in the chamber interior, whereby the elution buffer contains nucleic acids from the particulate sample.

Another aspect is for a process for collecting nucleic acids from a particulate sample comprising:
(a) transferring an aliquot of a particulate sample containing nucleic acids into a device comprising
(i) a chamber interior comprising a fibrous nucleic acid binding surface, the chamber interior being capable of expanding in size in at least one dimension; and
(ii) a nucleic acid binding solution; the fibers of the fibrous nucleic acid binding surface expanding to at least partially fill the chamber interior upon wetting with the particulate sample and the nucleic acid binding solution;
(b) exposing the device and its contents to ultrasound;
(c) mixing the particulate sample with the nucleic acid binding solution;
(d) expelling the nucleic acid binding solution from the device by compression of the fibrous nucleic acid binding surface while retaining the fibrous nucleic acid binding surface in the chamber interior;
(e) transferring an aliquot of elution buffer into the device;
(f) mixing the elution buffer with the fibrous nucleic acid binding surface; and
(g) expelling the elution buffer from the device by compression of the fibrous nucleic acid binding surface while retaining the fibrous nucleic acid binding surface in the chamber interior, whereby the elution buffer contains nucleic acids from the particulate sample.

A further aspect is for a process for collecting nucleic acids from a particulate sample comprising:
(a) mixing an aliquot of a particulate sample containing nucleic acids with a nucleic acid binding solution;
(b) exposing the mixture of step (a) to ultrasound;
(c) transferring the mixture of step (b) into a device comprising a chamber interior comprising a fibrous nucleic acid binding surface, the chamber interior being capable of expanding in size in at least one dimension; the fibers of the fibrous nucleic acid binding surface expanding to at least partially fill the chamber interior upon wetting with the mixture;
(d) expelling the mixture from the device by compression of the fibrous nucleic acid binding surface while retaining the fibrous nucleic acid binding surface in the chamber interior;
(e) powderizing the fibrous nucleic acid binding surface;
(f) contacting an elution buffer with the powderized nucleic acid binding surface; and
(g) separating the elution buffer from the powderized nucleic acid binding surface, whereby the elution buffer contains nucleic acids from the particulate sample.

An additional aspect is for a process for collecting nucleic acids from a particulate sample comprising:
(a) transferring an aliquot of a particulate sample containing nucleic acids into a device comprising
(i) a chamber interior comprising a fibrous nucleic acid binding surface, the chamber interior being capable of expanding in size in at least one dimension; and
(ii) a nucleic acid binding solution; the fibers of the fibrous nucleic acid binding surface expanding to at least partially fill the chamber interior upon wetting with the particulate sample and the nucleic acid binding solution;
(b) exposing the device and its contents to ultrasound;
(c) mixing the particulate sample with the nucleic acid binding solution;
(d) expelling the nucleic acid binding solution from the device by compression of the fibrous nucleic acid binding surface while retaining the fibrous nucleic acid binding surface in the chamber interior;
(e) powderizing the fibrous nucleic acid binding surface;
(f) contacting an elution buffer with the powderized nucleic acid binding surface; and
(g) separating the elution buffer from the powderized nucleic acid binding surface, whereby the elution buffer contains nucleic acids from the particulate sample.

Another aspect is for a process for collecting nucleic acids from a particulate sample comprising:
(a) transferring an aliquot of a particulate sample containing nucleic acids into a device comprising
  (i) a chamber interior comprising a fibrous nucleic acid binding surface, the chamber interior being capable of expanding in size in at least one dimension; and
  (ii) a nucleic acid binding solution; the fibers of the fibrous nucleic acid binding surface expanding to at least partially fill the chamber interior upon wetting with the particulate sample and the nucleic acid binding solution;
(b) mixing the particulate sample with the nucleic acid binding solution;
(c) expelling the nucleic acid binding solution from the device by compression of the fibrous nucleic acid binding surface while retaining the fibrous nucleic acid binding surface in the chamber interior;
(d) powderizing the fibrous nucleic acid binding surface;
(e) contacting an elution buffer with the powderized nucleic acid binding surface; and
(f) separating the elution buffer from the powderized nucleic acid binding surface, whereby the elution buffer contains nucleic acids from the particulate sample.

An additional aspect is for a process for collecting nucleic acids from a particulate sample comprising:
(a) exposing an aliquot of a particulate sample containing nucleic acids to a nucleic acid binding surface in the presence of a nucleic acid binding solution, said nucleic acid binding surface comprising a fibrous material capable of expansion upon wetting;
(b) binding the nucleic acids to the nucleic acid binding surface by expanding the fibrous material;
(c) separating the particulate sample from the nucleic acid binding surface comprising nucleic acids bound thereto by compression of the fibrous material;
(d) washing the nucleic acid binding surface with a wash solution whereby the fibrous material is again expanded;
(e) separating the wash solution from the nucleic acid binding surface comprising nucleic acids bound thereto by compression of the fibrous material;
(f) powderizing the nucleic acid binding surface;
(g) exposing an aliquot of elution buffer to the nucleic acid binding surface; and
(h) eluting nucleic acids from the nucleic acid binding surface.

Other objects and advantages will become apparent to those skilled in the art upon reference to the detailed description that hereinafter follows.

BRIEF DESCRIPTION OF THE FIGURES

General: BAX® system detection results are shown in many of the following figures. In all cases, the (+) signs are interpreted as a positive detection response for the target organism, the (−) signs are interpreted as a negative detection response, the (?) signals are interpreted as samples which encountered an error due to shutdown of the PCR reaction. On all PCR signal curves, the y-axis represents the relative fluorescence intensity, and the x-axis represents PCR cycle number. In general, increased intensity of the dashed ("Pathogen Target 1" or "PT1") or dotted ("Pathogen Target 2" or "PT2") target curves (a larger increase on the y-axis) is observed when the PCR reaction is more robust. This occurs because of increased target organism concentration, decreased PCR inhibition, or both.

FIG. 1: BAX® PCR Signal Curves for unsonicated ("Control") samples and samples sonicated ("Sonicated") with an ultrasonic horn for 30 sec. Shown in the graph is a representative fluorescence intensity measurement for samples spiked with one of two pathogen targets organisms (i.e., Pathogen Target 1 and Pathogen Target 2) at a concentration of 100 CFU/mL. The dashed line indicates the relative fluorescence intensity for Pathogen Target 1, and the dotted line indicates the relative fluorescence intensity for Pathogen Target 2. The solid black line indicates the relative fluorescence intensity for the internal control ("Internal Control" or "IC"). Each line on the y-axis represents a relative fluorescence intensity displayed in 0.1 unit increments, and each line of the x-axis represents 10 PCR cycles. The sonicated sample shows increased sensitivity, allowing 100 CFU/mL detection vs. control that does not. The inset is a results summary for samples sonicated with an ultrasonic horn compared to unsonicated samples. Samples were spiked with 0 CFU/mL ("Blank"), 100 CFU/mL, 125 CFU/mL, or 250 CFU/mL *E. coli* O157:H7. The (+) signs are interpreted as a positive detection response for the target organism, and the (−) signs are interpreted as a negative detection response.

FIG. 5: Crushing Quartzel® prior to elution allows detection of 100 CFU/mL *E. coli* O157:H7 in pure culture enrichments with no PCR shutdown. Shown in the graph is a representative fluorescence intensity measurement for pure culture enrichment samples ("pure culture") and ground beef matrix samples ("gb matrix") spiked with Pathogen Target 1 or Pathogen Target 2. The dashed line indicates the relative fluorescence intensity for Pathogen Target 1, and the dotted line indicates the relative fluorescence intensity for Pathogen Target 2. The solid black line indicates the relative fluorescence intensity for the Internal Control. Each line on the y-axis represents a relative fluorescence intensity displayed in 0.25 unit increments, and each line on the x-axis represents 10 PCR cycles. Samples were spiked with 100 CFU/mL pathogen. The inset is a results summary for samples spiked with 100 CFU/mL E. coli O157:H7 showing PCR detection in all six pure culture samples and four out of six gb matrix samples. The (+) signs are interpreted as a positive detection response for the target organism, the (−) signs are interpreted as a negative detection response, and the (?) signal is interpreted as a sample which encountered an error due to shutdown of the PCR reaction.

FIG. 6: Shown in the graph is a representative fluorescence intensity measurement for ground beef samples mixed with various silica capture substrate preparations (#1 to #5). Samples were spiked with Pathogen Target 1 or Pathogen Target 2. The dashed line indicates the relative fluorescence intensity for Pathogen Target 1, and the dotted line indicates the relative fluorescence intensity for Pathogen Target 2. The solid black line indicates the relative fluorescence intensity for the Internal Control. Each line on the y-axis represents a relative fluorescence intensity displayed in 0.1 unit increments, and each line on the x-axis represents 10 PCR cycles. All attempts to detect E. coli O157:H7 from ground beef utilizing a powdered silica capture substrate result in PCR shutdown. The inset is a results summary for ground beef samples spiked with pathogen and mixed with silica capture substrate preparations ("SiO2"). The (−) sign is interpreted as a negative detection response, and the (?) signals are interpreted as samples which encountered an error due to shutdown of the PCR reaction. All fifteen samples resulted in PCR shutdown.

DETAILED DESCRIPTION OF PREFERRED EMBODIMENTS

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Definitions

In this disclosure, a number of terms and abbreviations are used. The following definitions are provided.

As used herein, the term "about" or "approximately" means within 20%, preferably within 10%, and more preferably within 5% of a given value or range.

The term "comprising" is intended to include embodiments encompassed by the terms "consisting essentially of" and "consisting of". Similarly, the term "consisting essentially of" is intended to include embodiments encompassed by the term "consisting of".

"Polymerase chain reaction" is abbreviated PCR.

A "chaotrope" is any chemical substance which disturbs the ordered structure of liquid water. Chaotropes facilitate, e.g., unfolding, extension, dissociation of proteins, and the hydrogen boding of nucleic acids. Exemplary chaotropic salts include sodium iodide, sodium perchlorate, guanidinium thiocyanate, guanidinium isothiocyanate, and guanidinium hydrochloride.

The term "isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. The term also embraces recombinant polynucleotides and chemically synthesized polynucleotides.

The terms "polynucleotide", "polynucleotide sequence", "nucleic acid", "nucleic acid sequence", and "nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more strands of cDNA, genomic DNA, synthetic DNA, or mixtures thereof.

The term "silica" as used herein denotes materials which are mainly built up of silicon and oxygen. These materials comprise, for example, silica, silicon dioxide, silica gel, fumed silica gel, diatomaceous earth, celite, talc, quartz, crystalline quartz, amorphous quartz, glass, glass particles including all different shapes of these materials. Glass particles, for example, may comprise particles of crystalline silica, soda-lime glasses, borosilicate glasses, and fibrous, non-woven glass.

As used herein, "ultrasound" and "ultrasonic" generally refer to acoustic disturbances in a frequency range above about 20 kHz and which extend upwards to over 2 MHz.

Collection Methods

One embodiment disclosed herein relates to the use of ultrasonic energy to simultaneously shear large nucleic acid molecules and large particulates to very small sizes prior to or during a chemical binding step to a capture substrate. Another embodiment involves crushing the capture substrate prior to eluting the bound nucleic acid molecules to enable better wetting of the substrate and easier diffusion of bound nucleic acid molecules out of the substrate. The basic steps of disclosed herein are as follows.

1. To a container is added a particulate sample containing nucleic acids and a nucleic acid binding solution. In some embodiments, this solution is treated with ultrasonic energy and exposed (simultaneously, afterward, or both) to a fibrous nucleic acid binding surface. After mixing and brief exposure, the solution is expelled leaving behind the nucleic acids bound to the fibrous nucleic acid binding surface.
2. Optionally, wash the surface with solvents that remove proteins, fats, and other impurities that remain.
3. In some embodiments, crush the nucleic acid binding surface to generate a fine powder.
4. Release the nucleic acids with a buffer compatible with PCR amplification and fluorescent detection using a volume of buffer 10 to 10,000 times smaller than the original sample volume.

The disclosed collection methods result in a concentration of nucleic acids 10 to 10,000 times higher than in the original sample and without the presence of the PCR inhibitory components.

As noted above, in embodiments employing ultrasonic energy to shear large nucleic acids and reduce the size of particulates, the ultrasonic energy can be employed simultaneous with or after exposure to a nucleic acid binding surface. Co-owned, co-pending PCT Application No. PCT/US2010/044083, discloses separation of nucleic acids from particulate samples using nucleic acid binding surface fibers. As discussed therein, a particulate sample may be mixed with nucleic acid binding surface fibers in a chamber, and when that chamber is compressed and its contents released through an orifice, the fibers remain in the chamber whereas the particles are expelled. If this process is performed in the presence of a chaotrope, the nucleic acid binding surface fibers expand during mixing to infiltrate the bulk of the particulate sample and collect a substantial portion of the nucleic acids. Also, after expulsion of liquids in the chamber, wash volumes may be introduced to the fiber with the nucleic acid binding surface fibers again expanding to the volume. When these wash volumes are expelled, remaining particulates are also expelled resulting in a small, compressed, mass of nucleic acid binding surface fibers being a very small volume of the original enrichment and presenting most of the target nucleic acids. The nucleic acids may be released from the nucleic acid binding surface fiber surface into a small volume of eluent producing a large concentration amplification of the target.

Ultrasound used in accordance with this invention consists of sound-like waves whose frequency is above the range of normal human hearing, i.e., above 20 kHz (20,000 cycles per second). Ultrasonic energy with frequencies as high as 10 gigahertz (10,000,000,000 cycles per second) has been generated, but for the purposes of this invention, useful results will be achieved with frequencies within the range of from about 20 kHz to about 2.5 Mhz, preferably of about 20 kHz to about 100 kHz. Ultrasonic waves can be generated from mechanical, electrical, electromagnetic, or thermal energy sources.

The intensity of the sonic energy may vary widely. For the purposes of this invention, best results will generally be achieved with an intensity ranging from about 1 W/cm$^2$ to about 30 W/cm$^2$. The typical electromagnetic source is a magnetostrictive transducer which converts magnetic energy into ultrasonic energy by applying a strong alternating magnetic field to certain metals, alloys and ferrites. The typical electrical source is a piezoelectric transducer, which uses natural or synthetic single crystals (such as quartz) or ceramics (such as barium titanate or lead zirconate) and applies an alternating electrical voltage across opposite faces of the crystal or ceramic to cause an alternating expansion and contraction of crystal or ceramic at the impressed frequency. The various methods of producing and applying ultrasonic energy, and commercial suppliers of ultrasound equipment, are well known among those skilled in ultrasound technology.

The residence time of exposure of the particulate sample to ultrasound is not critical to the practice or the success of the invention, and the optimal residence time will vary according to the type of particulate sample being treated. Best results, however, will generally be obtained with residence times ranging from about 1 second to about 2 minutes, preferably about 1 second to about 30 seconds.

In one embodiment, an aliquot of a particulate sample containing nucleic acids is transferred into a device comprising a chamber interior comprising a fibrous nucleic acid binding surface, the chamber interior being capable of expanding in size in at least one dimension; and a nucleic acid binding solution; the fibers of the fibrous nucleic acid binding surface expanding to at least partially fill the chamber interior upon wetting with the particulate sample and the nucleic acid binding solution. A typical sample enrichment protocol for diarrheagenic E. coli is described in the Bacteriological Analytical Manual, "BAM" (U.S. Food and Drug Administration): Aseptically weigh 25 g of sample into 225 ml of Brain Heart Infusion (BHI) broth (dilution factor of 1:10). If necessary, sample size may deviate from 25 g depending on availability of the sample, as long as the diluent is adjusted proportionally. Blend or stomach briefly. Incubate the homogenate for 10 min at room temperature with periodic shaking then allow the sample to settle by gravity for 10 min. Decant medium carefully into a sterile container and incubate for 3 h at 35° C. to resuscitate injured cells. Transfer contents to 225 mL double strength Tryptone Phosphate (TP) broth in a sterile container and incubate 20 h at 44.0±0.2° C. It is noted, however, that any sample enrichment procedure can be utilized in the present processes.

Inside the chamber resides a fibrous nucleic acid-binding surface. Preferably, the fibrous nucleic acid-binding surface is non-magnetic. In some embodiments this fibrous nucleic acid-binding surface is a clean silica surface, with some embodiments utilizing a clean, activated silica surface. Cleaning and activation of the silica is effectuated, e.g., by washing with hydrochloric acid although a separate cleaning step may not be required for all silica types. Following the cleaning step the cleaning solution is expelled and the enriched particulate sample, e.g. a food sample, clinical sample, environmental sample, or a research sample, containing nucleic acids is aspirated.

Alternatively, the nucleic acid-binding surface can be, e.g., NOMEX® fibers (meta-aramid; E.I. du Pont de Nemours & Co., Wilmington, Del.), KEVLAR® (para-aramid; E.I. du Pont de Nemours & Co., Wilmington, Del.), a polyamide, e.g., nylon (e.g., nylon 6,6, nylon 6, nylon 11, nylon 12, nylon 612).

In embodiments utilizing ultrasound after exposure to a nucleic acid binding surface, ultrasonic energy can be applied directly to the chamber containing the nucleic acid binding surface. In embodiments where the chamber is a plastic syringe or plastic vial, a one inch diameter cylindrical horn can be used, with a tip that has been machined to match the profile of the end of a syringe or vial. This is done to ensure maximum contact between the horn and the syringe to maximize the transfer of sound energy into the fluid (see co-owned, co-filed, U.S. Patent Application Ser. No. 61/452,683, incorporated herein by reference). If a vial is used, the horn tip can be machined to match the profile of the end of the vial. To improve energy transfer, fluids such as oils can be used to improve sound coupling.

An alternate embodiment uses an ultrasonic transducer, booster, horn, and anvil to clamp a liquid filled syringe or vial in a way that transmits sound energy into the side of the syringe or vial. The horn tip and mating anvil have a semi-cylindrical cut in their ends that is transverse to the horn and transducer axis and whose radius is matched to the syringe or vial cylindrical radius. The diameter of the horn is adjusted to match the height of the liquid in the syringe or vial.

Preferably, ultrasonic energy is applied to the outside of the chamber, the sound thereby be conducted through the chamber wall, to avoid, for example, cross-contamination when multiple samples are involved. Applying the ultrasonic energy to the outside of the chamber also has the advantage of avoiding the need to clean the ultrasound-generating device between samples.

Typically, the volume of sample may range from 500 μL to 10 mL or higher depending on sample type. An equal volume of nucleic acid binding solution containing, in some embodiments, detergent, ethylenediaminetetraacetic acid (EDTA), buffering components and possibly other components to facilitate binding and lysis is then aspirated with the sample. The nucleic acid binding solution is typically a chaotropic salt but alternatively can be a blend of salts such as 6 M NaClO$_4$, Tris, and trans-1,2-cyclohexanediaminetetraacetic acid (CDTA); or 8M NaClO$_4$ and Tris at pH 7.5; or NaI.

The solutions within the chamber are mixed thoroughly (on, for example, a vortex mixer) causing the fibrous nucleic acid-binding surface to disperse fully and expose the bulk of its surface area throughout the liquid in the chamber. The device is then incubated during which time cell lysis (if cells are present) and nucleic acid binding occurs. An exemplary mixing condition is at room temperature for 15 minutes on a rotating mixer.

After mixing, the nucleic acid binding solution is expelled from the device by compression of the fibrous nucleic acid binding surface while retaining the fibrous nucleic acid binding surface in the chamber interior.

As an example, using the chamber described above, an aliquot of a food sample incubation broth containing microorganisms is pulled into the chamber of the device, and the broth is mixed with the nucleic acid binding solution within the chamber. After mixing, the nucleic acid binding solution is expelled from the chamber, but nucleic acids within the microorganisms bind to the fibrous nucleic acid-binding surface and are thereby retained within the chamber.

In some embodiments, the fibrous nucleic acid binding surface can then be washed with a wash solution. Following the initial sample incubation after the liquid is expelled from the device, an equal volume of wash buffer containing the nucleic acid binding solution, detergent, and buffering salts can be aspirated into the device. The device can then be mixed, e.g., on a vortex mixer as before, to expose fully the fibrous nucleic acid binding surface, and the wash fluid is then immediately expelled, while retaining the fibrous nucleic acid binding surface in the chamber interior.

Further, an equal volume of ethanol (e.g., 70% ethanol) can then be aspirated, mixed as before, and expelled. Next, an equal volume of acetone can be aspirated, mixed as before, and expelled.

The wash solution is selected such that a release of the nucleic acids from the fibrous nucleic acid binding surface preferably does not take place—or at least not in any significant amount—yet any impurities present are washed out as well as possible. The contaminated wash solution is preferably removed in the same manner as the nucleic acid binding solution at the end of the binding of the nucleic acids.

Any conventional wash buffer or any other suitable medium can be used as wash solution. Generally buffers with low or moderate ionic strength are preferred such as, for example, 10 mM Tris-HCl at a pH of 8, 0-10 mM NaCl. In addition, however, wash buffers that have higher salt concentrations—such as, for example, 3M guanidinium hydrochloride—can also be used. Equally, other standard media for carrying out the washing step can be used, for example acetone or alcohol containing media such as, for example, solutions of lower alkanols with one to five carbon atoms, preferably solutions of ethanol in water and especially preferred aqueous 70% ethanol. In another preferred embodiment, the wash solution is isopropanol.

In some embodiments, the washing solution is characterized in that the nucleic acid binding solution, particularly a chaotropic substance, is not contained therein. As a result, a possibility of having the chaotropic substance incorporated into a recovery step after the washing step can be reduced. In the elution step, where the chaotropic substance is incorporated thereinto, the chaotropic substance sometimes hinders a later enzyme reaction such as PCR reaction or the like; therefore considering the later enzyme reaction, not including the chaotropic substance to a washing solution is preferable.

Following expulsion of the nucleic acid binding solution from the chamber, or following the optional wash step(s) if utilized, the fibrous nucleic acid binding surface can be dried by placing the device in, e.g., a heat block (e.g., at 55° C. for 15 minutes). In another embodiment, the optional drying step can be performed by use of a vacuum.

After the optional washing and/or drying steps, the fibrous nucleic acid binding surface can be powderized to enable better wetting of the nucleic acid binding surface and easier diffusion of bound nucleic acid molecules out of the nucleic acid binding surface. The powderization step produces a plurality of fine powders. Preferably, the average particle long axis length will be reduced to below about 20 µm. It is possible to powderize the nucleic acid bind surface by employing a conventionally publicly-known method such as crushing, grinding, shearing, pulverizing, cutting, shredding, hammering, sanding, milling, or a combination thereof. In a preferred embodiment, the nucleic acid binding surface is crushed into a powder by placing the nucleic acid binding surface into a chamber (e.g., a spin column) and pulverizing the nucleic acid binding surface with a pestle-like device (in the case of a spin column, a syringe plunger with a sharp surface can be used).

The captured nucleic acid is eluted by exposure to a small volume (e.g., 70-100 µl) of an elution buffer. A typical elution buffer is a PCR buffer solution pH 8.3 containing all the necessary components for PCR (i.e., MgCl$_2$, buffering salts, etc.) but not containing a chaotropic salt. The selection of the elution buffer is determined in part by the contemplated use of the isolated nucleic adds. Examples of suitable elution buffers are TE buffer, aqua bidest and PCR buffer. It is preferred that pH of a elution solution is 2 to 11 and, more preferably, 5 to 9. In addition, ionic strength and salt concentration particularly affect the elution of adsorbed nucleic acid. Preferably, the elution solution has an ionic strength of 290 mmol/L or less and has a salt concentration of 90 mmol/L or less. As a result thereof, recovering rate of nucleic acid increases and much more nucleic acid is able to be recovered.

When mixing is complete, the elution buffer is expelled from the device, with the elution buffer containing nucleic acids that previous were bound to the nucleic acid-binding surface. As necessary, additional elution buffer can be pulled into the device, mixed with the nucleic acid-binding surface, and expelled from the device to maximize recovery of bound nucleic acids. Because the solution resulting from the contact with the nucleic acid-binding surface contains the adsorbed nucleic acids, the recovered solution is typically subjected to a following step, for example PCR amplification of the nucleic acids.

Also, in the elution step, it is possible to add a stabilizing agent for preventing degradation of nucleic acid recovered in the elution solution of nucleic acid. As the stabilizing agent, an antibacterial agent, a fungicide, a nucleic acid degradation inhibitor and the like can be added. As the nuclease inhibitor, EDTA and the like can be cited.

There is no limitation for the infusing times for a elution buffer and that may be either once or plural times. Usually, when nucleic acid is to be separated and purified quickly and simply, that is carried out by means of one recovery while, when a large amount of nucleic acid is to be recovered, elution buffer may be infused for several times.

By way of the above methods, nucleic acids can be recovered from a myriad of microorganisms including, e.g., bacteria, fungi, algae, or viruses.

EXAMPLES

The present invention is further defined in the following Examples. It should be understood that these Examples, while indicating preferred embodiments of the invention, are given by way of illustration only.

The meaning of abbreviations is as follows: "h" means hour(s), "min" means minute(s), "sec" means second(s), "d" means day(s), "mL" means milliliter(s), "µL" means microliter(s), "CFU" means colony forming unit(s), "MP" means multiplex, "BHI" means brain heart infusion, "BPW" means buffered peptone water, "n.d." means no data, "EDTA" means ethylenediaminetetraacetic acid.

Example 1

25 g of ground beef was stomached for 30 sec and enriched in 225 mL of MP media (BAX® System MP Media for *E. coli* O157:H7, DuPont Qualicon, Wilmington, Del.) overnight. Various aliquots of this enrichment were spiked with several concentrations of *E. coli* O157:H7. 2 mL of the ground beef enrichment was mixed with 1 mL of a chaotropic binding buffer solution (5.2 M guanidinium thiocyanate, 22 mM EDTA, 1.3% by weight Triton X-100 in 50 mM Tris-Cl pH 6.4) in a 15 mL falcon tube and sonicated for 30 sec with either an ultrasonic water bath (relatively low energy sonication) or an ultrasonic horn (relatively high energy sonication) or not at all (controls). The sonicated solution was added to a 5 mL polypropylene syringe which contained 10 mg of Quartzel® wool (4 µm fiber size (Saint-Gobain Quartz, Northboro, Mass.)). The sample was left in contact with the Quartzel® wool for five minutes, and was ejected from the syringe manually. Next, 3 mL of isopropanol was added to the syringe (which still contains the Quartzel® wool). The isopropanol wash was held in the syringe for 1 minute, and finally removed from the syringe via a vacuum manifold. Active vacuum was pulled on the syringe (with plunger removed) for 5 minutes to ensure that the Quartzel® wool was dry. 100 µL of BAX® lysis buffer was added to the Quartz wool and allowed to sit for 5 minutes. The buffer was finally ejected from the syringe by depressing a clean plunger into the syringe. This solution was used for standard RT BAX® PCR-based detection of *E. coli* O157:H7.

Figure 1:
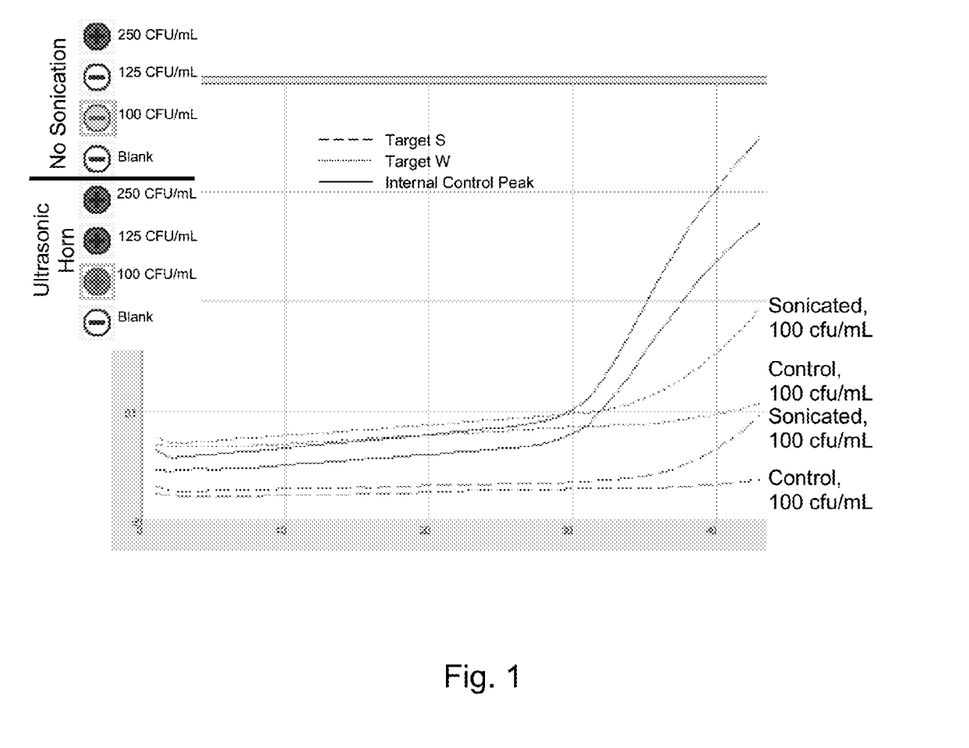
Figure 2:
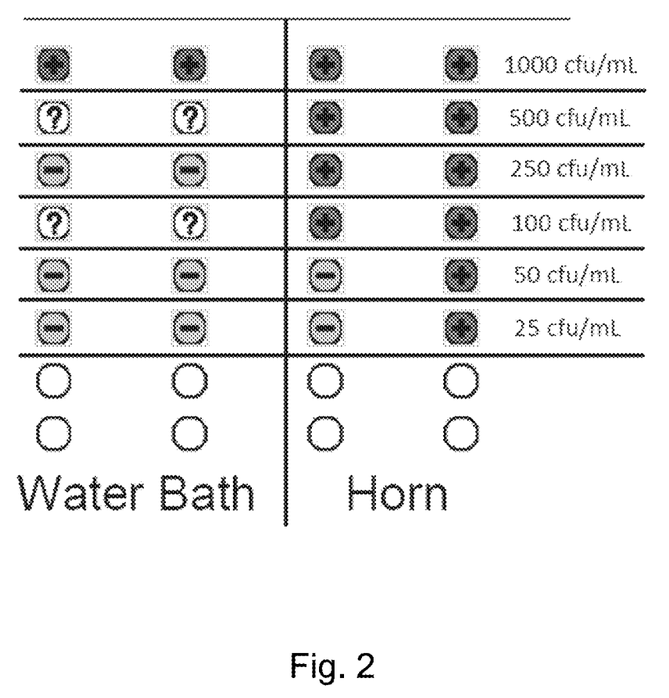
FIG. 2: *E. coli* O157:H7 detection results from RT BAX® in samples that were lightly sonicated in a water bath ("Water Bath"), and those aggressively sonicated by an ultrasonic horn ("Horn"). Samples were spiked with 25 CFU/mL, 50 CFU/mL, 100 CFU/mL, 250 CFU/mL, 500 CFU/mL, or 1000 CFU/mL *E. coli* O157:H7. Samples experiencing less ultrasonic energy did not display detection below 1000 CFU/mL, and showed some PCR shutdown. Samples sonicated with an ultrasonic horn show detection as low as 25 CFU/mL, and do not display PCR shutdown. The (+) signs are interpreted as a positive detection response for the target organism, the (−) signs are interpreted as a negative detection response, and the (?) signals are interpreted as samples which encountered an error due to shutdown of the PCR reaction.

Ultrasonic treatment of food enrichment samples prior to DNA extraction and concentration shows a dramatic improvement in PCR signal (FIGS. 1 and 2) and Inhibition (FIG. 2).

Comparative Example 1

25 g of ground beef was stomached for 30 sec and enriched in 225 mL of MP media overnight. Various aliquots of this enrichment were spiked with several concentrations of *E. coli* O157:H7. 2 mL of the ground beef enrichment was mixed with 1 mL of a chaotropic binding buffer solution in a 3 mL polypropylene syringe which contained 10 mg of Quartzel® wool (4 µm fiber size). The sample was left in contact with the Quartzel® wool for five minutes, and was ejected from the syringe manually. Next, 3 mL of isopropanol was added to the syringe (which still contains the Quartzel® wool). The isopropanol wash was held in the syringe for 1 minute, and finally removed from the syringe via a vacuum manifold. Active vacuum was pulled on the syringe (with plunger removed) for 5 minutes to ensure that the Quartzel® wool was dry. 100 µL of BAX® lysis buffer was added to the Quartz wool—some samples were sonicated by external syringe contact with an ultrasonic horn while controls were not. All samples were allowed to sit for 5 minutes. The buffer was finally ejected from the syringe by depressing a clean plunger into the syringe. This solution was used for standard RT BAX® PCR-based detection of *E. coli* O157:H7.

Figure 3:
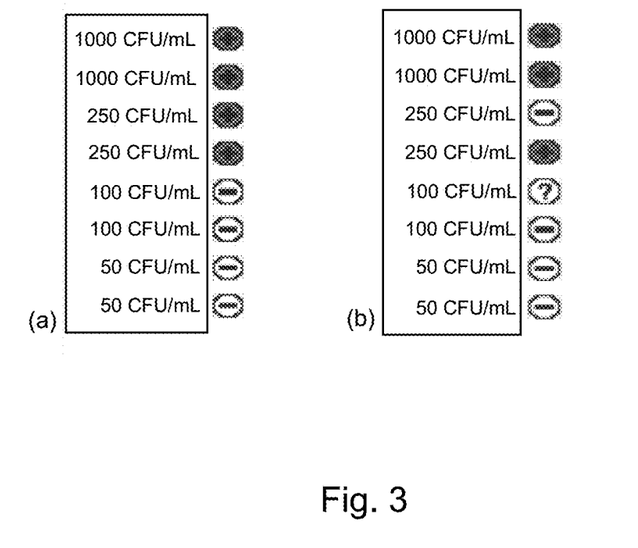
FIG. 3: BAX® Results from (a) control samples and (b) samples which were sonicated just prior to elution. Samples were spiked with 50 CFU/mL, 100 CFU/mL, 250 CFU/mL, 500 CFU/mL, or 1000 CFU/mL *E. coli* O157:H7. No increase in process performance is observed. The (+) signs are interpreted as a positive detection response for the target organism, the (−) signs are interpreted as a negative detection response, and the (?) signal is interpreted as a sample which encountered an error due to shutdown of the PCR reaction.

Sonication of sample just prior to elution does not improve efficiency (FIG. 3).

Example 2

For each sample, 1 mL *E. coli* DNA (5 ng/µl, Type VIII, 15-113 kbp, Sigma) was mixed with 1 mL L6 Buffer and added into the syringes devices. Each syringe device contained ten 1 mg pieces of 4 µm Quartzel® fiber. Devices were capped, inverted eight times to mix, and sat for 5 min at room temperature. The caps were removed and samples were allowed to drain by passive flow. Fibers were washed with 3 mL of isopropanol and dried by vacuum for 5 min. Each fiber was then transferred into a Pierce Handee microfuge column (#89868, Thermo Scientific, Rockford, Ill.) containing a 30 µm pore size filter that would retain the fiber after centrifugation. For three of the six the samples, fibers were ground into a powder using a pipet tip. One hundred twenty microliters of 10 mM Tris-Cl pH 8.5 were added to each fiber and samples sat for 5 min at room temperature to elute the DNA. The columns were then centrifuged for 30 sec at 10000 rpm to collect the eluate. Another 120 µL elution buffer was added and samples sat again for 5 min. Samples were then spun and the eluted DNA was collected into fresh tubes. Twenty microliters of the samples were run on a 1% agarose gel stained with ethidium bromide. The DNA yield was also quantified by optical density (OD260) and expressed as percent recovery.

Figure 4:
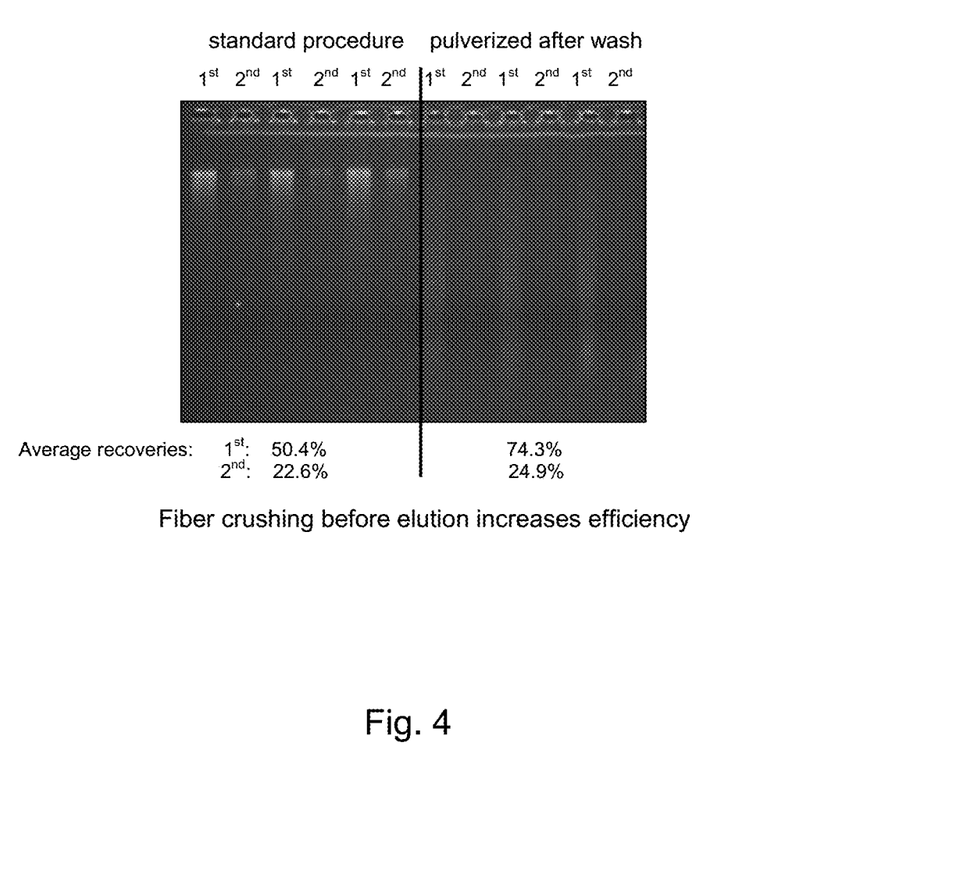
FIG. 4: Agarose gel picture and average recoveries showing crushing Quartzel® prior to elution resulted in DNA shearing and increased elution efficiency.

Results are shown in FIG. 4. The pulverized fiber/DNA resulted in the expected DNA shearing and also in higher DNA recovery with the first elution.

Example 3

25 g of ground beef was stomached for 30 sec and enriched in 225 mL of MP media overnight. Various aliquots of this enrichment were spiked with several concentrations of *E. coli* O157:H7. 2 mL of the ground beef enrichment was mixed with 1 mL of a chaotropic binding buffer solution and added to a 5 mL polypropylene syringe which contained 10 mg of Quartzel® wool (4 µm fiber size). The sample was left in contact with the Quartzel® wool for five minutes, and was ejected from the syringe manually. Next, 3 mL of isopropanol was added to the syringe (which still contains the Quartzel® wool). The isopropanol wash was held in the syringe for 1 minute, and finally removed from the syringe via a vacuum manifold. Active vacuum was pulled on the syringe (with plunger removed) for 5 minutes to ensure that the Quartzel® wool was dry. Next, the Quartzel® wool was moved into a Qiagen DNEasy spin column and crushed and pulverized with a syringe plunger that had been scratched with a blade (so that it was rough and sharp). The crushing procedure involved squeezing the wool in the column and turning the plunger 10x. The wool would become like a powder during this process. 100 µL of BAX® lysis buffer was added to the Quartz wool and allowed to sit for 5 minutes. The buffer was finally ejected from the syringe by depressing a clean plunger into the syringe. This solution was used for standard RT BAX® PCR-based detection of *E. coli* O157:H7.

Figure 5:
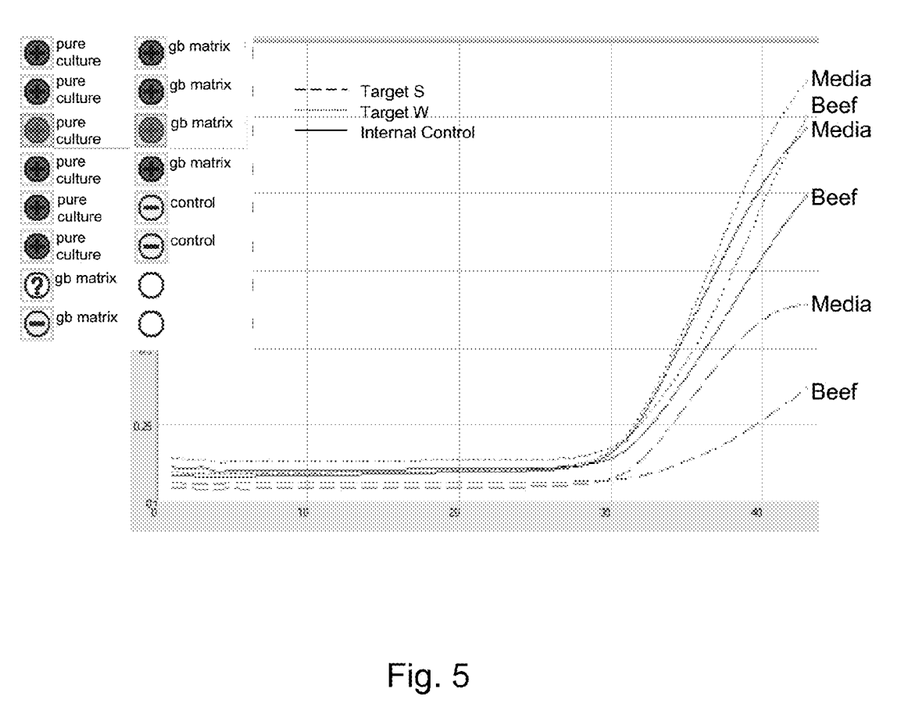

Crushing fiber prior to elution allows 100 CFU/mL detection of *E. coli* O157:H7 in ground beef (FIG. 5).

Comparative Example 2

25 g of ground beef was stomached for 30 sec and enriched in 225 mL of MP media overnight. Various aliquots of this enrichment were spiked with several concentrations of *E. coli* O157:H7. 2 mL of the ground beef enrichment was mixed with 1 mL of a chaotropic binding buffer solution in a 3 mL microcentrifuge tube containing 10 mg of vitreous silica (Sigma, 0.5-10 μm particle diameter). The tube was vortexed and held for 5 minutes, then spun down at 10000 rpm for 30 sec to pellet the silica. The supernatant was removed, and an attempt was made to resuspend the pellet in 3 mL isopropanol via vortexing. The pellet would not resuspend well, and was spun down again at 10000 rpm for 30 sec. The isopropanol was decanted off, and the pellet again washed with isopropanol by the same procedure. Next, the silica powder was dried in a heat block at 80° C. for 30 minutes to ensure removal of all isopropanol. Finally, the silica was exposed to 100 μL of BAX® lysis buffer, vortexed for 30 sec, and incubated at room temp for 5 minutes. The silica was spun down one final time at 10000 rpm for 30 sec, and 30 μL of the solution was decanted from above the silica pellet and used in standard *E. coli* real-time BAX® protocols.

Figure 6:
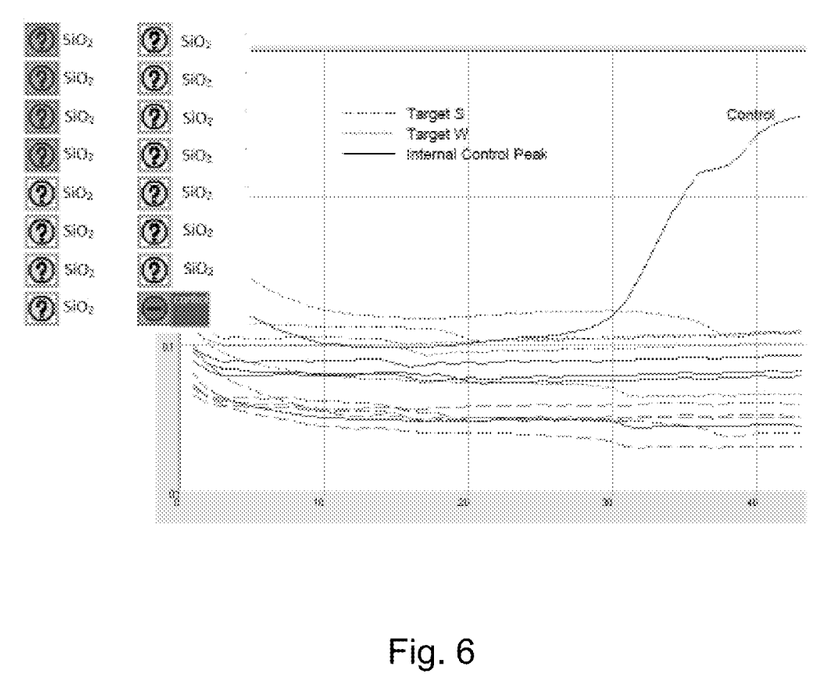

The results are shown in FIG. 6, which show major issues with PCR shutdown.

Example 4

25 g of ground beef was stomached for 30 sec and enriched in 225 mL of MP media for 6 h. Various aliquots of this enrichment were spiked with several concentrations of *E. coli* O157:H7. 2 mL of the ground beef enrichment was mixed with 1 mL of a chaotropic binding buffer solution in a 5 mL PP tube and sonicated for 30 sec with an ultrasonic horn (relatively high energy sonication). The sonicated solution was added to a 5 mL polypropylene syringe which contained 10 mg of Quartzel® wool (4 μm fiber size). The sample was left in contact with the Quartzel® wool for five minutes, and was ejected from the syringe manually. Next, 3 mL of isopropanol was added to the syringe (which still contains the Quartzel® wool). The isopropanol wash was held in the syringe for 1 minute, and finally removed from the syringe via a vacuum manifold. Active vacuum was pulled on the syringe (with plunger removed) for 5 minutes to ensure that the Quartzel® wool was dry. Next, the Quartzel® wool was moved into a Qiagen DNEasy spin column and crushed and pulverized with a syringe plunger that had been scratched with a blade (so that it was rough and sharp). The crushing procedure involved squeezing the wool in the column and turning the plunger 10×. The wool would become like a powder during this process. 100 μL of BAX® lysis buffer was added to the Quartz wool and allowed to sit for 5 minutes. The buffer was finally ejected from the syringe by centrifugation at 10000 rpm for 30 sec. This solution was used for standard RT BAX® PCR-based detection of *E. coli* O157:H7.

Figure 7:
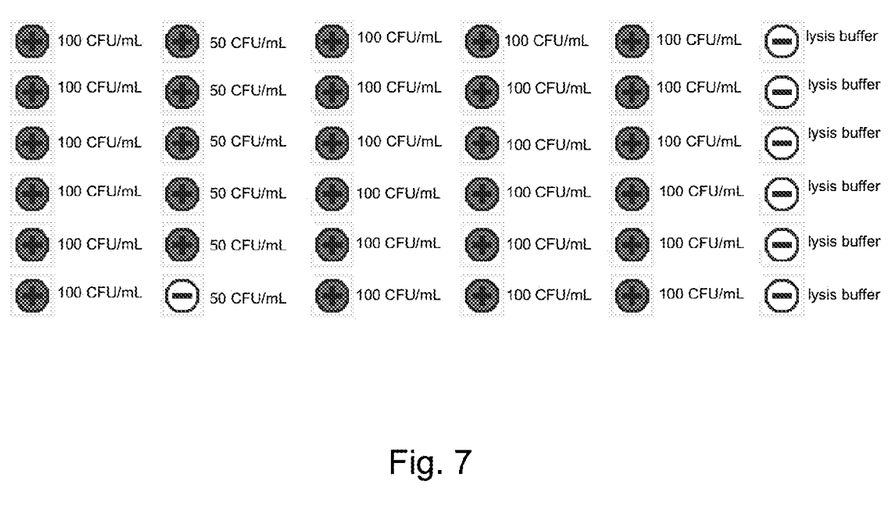
FIG. 7: Combined ultrasonic treatment and substrate crushing allows excellent detection at 100 CFU/mL cell loading (24/24 attempts), and good detection at 50 CFU/mL cell loading (5/6 attempts). The (+) signs are interpreted as a positive detection response for the target organism, and the (−) signs are interpreted as a negative detection response.

Samples prepared utilizing ultrasonic treatment and substrate crushing demonstrate excellent detection capability (FIG. 7).

What is claimed is:

1. A process for collecting nucleic acids from a particulate sample comprising:
   (a) transferring an aliquot of a particulate sample containing nucleic acids into a device comprising
      (i) a chamber interior comprising a fibrous nucleic acid binding surface, the chamber interior being capable of expanding in size in at least one dimension; and
      (ii) a nucleic acid binding solution;
      the fibers of the fibrous nucleic acid binding surface expanding to at least partially fill the chamber interior upon wetting with the particulate sample and the nucleic acid binding solution;
   (b) mixing the particulate sample with the nucleic acid binding solution;
   (c) expelling the nucleic acid binding solution from the device by compression of the fibrous nucleic acid binding surface while retaining the fibrous nucleic acid binding surface in the chamber interior;
   (d) powderizing the fibrous nucleic acid binding surface;
   (e) contacting an elution buffer with the powderized nucleic acid binding surface; and
   (f) separating the elution buffer from the powderized nucleic acid binding surface, whereby the elution buffer contains nucleic acids from the particulate sample.

2. The process of claim 1 further comprising after step (c) and before step (d) the further steps of:
   washing the fibrous nucleic acid binding surface with a wash solution; and expelling the wash solution by compression of the fibrous nucleic acid binding surface while retaining the fibrous nucleic acid binding surface in the chamber interior.

3. The process of claim 2, wherein the expelling is performed by vacuum.

4. The process of claim 1, wherein the expelling of step (c) is performed by vacuum.

5. The process of claim 1, wherein the fibrous nucleic acid binding surface is non-magnetic.

6. The process of any of claims 1-5, wherein the fibrous nucleic acid binding surface is a clean silica surface.

7. The process of claim 6, wherein the clean silica surface is a clean, activated silica surface.

8. The process of claim 7, wherein the clean, activated silica surface comprises silica wool.

9. The process of any of claims 1-5, wherein the nucleic acid binding solution comprises a chaotropic salt.

10. The process of any of claims 1-5, wherein the particulate sample comprises eukaryotic cells, prokaryotic cells, viruses, and a combination thereof.

11. The process of any of claims 1-5, wherein the particulate sample is a food sample or a clinical sample.

12. The process of any of claims 1-5 further comprising after step (c) and before step (d) the further step of removing the fibrous nucleic acid binding surface from the device.

13. A process for collecting nucleic acids from a particulate sample comprising:
   (a) exposing an aliquot of a particulate sample containing nucleic acids to a nucleic acid binding surface in the presence of a nucleic acid binding solution, said nucleic acid binding surface comprising a fibrous material capable of expansion upon wetting;
   (b) binding the nucleic acids to the nucleic acid binding surface by expanding the fibrous material;
   (c) separating the particulate sample from the nucleic acid binding surface comprising nucleic acids bound thereto by compression of the fibrous material;
   (d) washing the nucleic acid binding surface with a wash solution whereby the fibrous material is again expanded;
   (e) separating the wash solution from the nucleic acid binding surface comprising nucleic acids bound thereto by compression of the fibrous material;
   (f) powderizing the nucleic acid binding surface;
   (g) exposing an aliquot of elution buffer to the powderized nucleic acid binding surface; and
   (h) eluting nucleic acids from the powderized nucleic acid binding surface.

14. The process of claim 13, wherein the fibrous nucleic acid binding surface is non-magnetic.

* * * * *